(12) United States Patent
Wang et al.

(10) Patent No.: US 12,043,649 B2
(45) Date of Patent: Jul. 23, 2024

(54) PECTIN METHYLESTERASE INHIBITOR GENE GhPMEI39 AND APPLICATION OF ITS ENCODED PROTEIN

(71) Applicant: INSTITUTE OF COTTON RESEARCH OF CAAS, Henan Province (CN)

(72) Inventors: Zhi Wang, Henan Province (CN); Fuguang Li, Henan Province (CN); Zhenzhen Wei, Henan Province (CN); Yonghui Li, Henan Province (CN)

(73) Assignee: INSTITUTE OF COTTON RESEARCH OF CAAS, Henan Province (CN)

( * ) Notice: Subject to any disclaimer, the term of this patent is extended or adjusted under 35 U.S.C. 154(b) by 0 days.

(21) Appl. No.: 18/549,749

(22) PCT Filed: Aug. 2, 2022

(86) PCT No.: PCT/CN2022/109760
§ 371 (c)(1),
(2) Date: Sep. 8, 2023

(87) PCT Pub. No.: WO2023/011487
PCT Pub. Date: Feb. 9, 2023

(65) Prior Publication Data
US 2024/0092842 A1    Mar. 21, 2024

(30) Foreign Application Priority Data
Aug. 2, 2021    (CN) .......................... 202110879491.1

(51) Int. Cl.
*C07K 14/415*    (2006.01)
*C12N 15/82*    (2006.01)

(52) U.S. Cl.
CPC ........ *C07K 14/415* (2013.01); *C12N 15/8262* (2013.01); *C12N 15/827* (2013.01)

(58) Field of Classification Search
None
See application file for complete search history.

(56) References Cited

U.S. PATENT DOCUMENTS

2012/0117691 A1    5/2012    Wang et al.
2016/0115499 A1    4/2016    Cui et al.

FOREIGN PATENT DOCUMENTS

| CN | 101824433 A | 9/2010 |
|---|---|---|
| CN | 103789330 A | 5/2014 |

(Continued)

OTHER PUBLICATIONS

English language machine translation of Hou et al. (CN110734910 published Jan. 31, 2020, 13 total pages). (Year: 2020).*

(Continued)

*Primary Examiner* — Matthew R Keogh
*Assistant Examiner* — Rebecca Stephens
(74) *Attorney, Agent, or Firm* — MUNCY, GEISSLER, OLDS & LOWE, PC (57) ABSTRACT

The present disclosure relates to the field of regulation of plant performance genes, in particular to a pectin methylesterase inhibitor gene GhPMEI39 and application of its encoded protein. The gene sequence of the pectin methylesterase inhibitor gene GhPMEI39 is shown in SEQ ID NO:1. According to the present disclosure, a public database is used to screen target genes, primers are designed to clone the target genes, its cotton transgenic materials and *Arabidopsis thaliana* transgenic materials are constructed, and plant development phenotypes after overexpression and constitutive expression of pectin methylesterase inhibitor protein are analyzed, and the role of the pectin methyl- (Continued)

esterase inhibitor gene GhPMEI39 in related functions such as plant flowering and inflorescence morphology is verified.

2 Claims, 6 Drawing Sheets

Specification includes a Sequence Listing.

(56) References Cited

FOREIGN PATENT DOCUMENTS

| CN | 106755004 A | | 5/2017 |
|---|---|---|---|
| CN | 110734910 | * | 1/2020 |
| CN | 110734910 A | | 1/2020 |
| CN | 113481211 A | | 10/2021 |
| WO | WO2005005470 A2 | | 1/2005 |

OTHER PUBLICATIONS

Etchells & Turner ("The PXY-CLE41 receptor ligand pair defines a multifunctional pathway that controls the rate and orientation of vascular cell division" 2010 Development 137(5):767-774). (Year: 2010).*

Genbank, Apr. 25, 2021, Predicted: Gossypium hirsutum uncharacterized LOC107962267 (LOC107962267), mRNA, XM_016898587. 2.

Pinzon-Latorre et al., Aug. 14, 2014, Pectinmethylesterases (PME) and Pectinmethylesterases inhibitors (PMEI) Enriched during Phloem Fiber Development in Flax (*Linum usitatissimum*), PLoS One, e105386:1-17.

Mei-Ling et al., Dec. 31, 2017, Identification and expression analysis of the gene family of Pectin methylesterase inhibitors (PMEI), Plant Physiology Journal, pp. 1988-1996.

Suzuki et al., Transcriptone analysis of cytoplasmic male sterility and restoration in CMS-D8 cotton, Plant Cell Rep, vol. 32, Jun. 7, 2013., pp. 1531-1542.

Lui et al., Cloning and Characterization of a Pectin Methylesterase Gene BrPMEI in Chinese Cabbage, Scientia Agricultura Sinica, vol. 44, No. 2, Dec. 31, 2011, pp. 325-334.

Liu et al., Pectin Methylesterase and pectin Remodelling Differ in the Fibre walls of two *Gossypium* species with very Different Fibre Properties, LOS One, vol. 8, No. 6, Jun. 30, 2013, e65131:1-13.

* cited by examiner

```
                              SEQUENCE LISTING

Sequence total quantity: 7
SEQ ID NO: 1           moltype = DNA  length = 549
FEATURE                Location/Qualifiers
source                 1..549
                       mol_type = other DNA
                       organism = synthetic construct
SEQUENCE: 1
atgggaattc tcttgcctcc ttgctatctt actctttttc tcctcctttt catctcattc    60
aacaatgtcg gccatcgaaa cctcgttttc gccaacgatg ccctgattga agcccaatgt   120
cacaatgctg aagtccccga aacctgcata aaatgcgtaa aatctgattc tcgaagtcaa   180
tcagccaata aagttggcat tgctgccatc atcataactt gtcttagcaa caaagccacg   240
accttgataa acaacatgac gactcttgct tcgggcgctc gcgacaagaa cttgaaagtg   300
gctctccgag gttgcgagaa agggttttac tacacgaaaa ccaatttgat cgctgcgacg   360
aaccgattga aggggaaaga atatgatcaa acgaatcttc tggtgaaaca agcgctcgaa   420
gaagaatttg tttgtaagat gaaagtggag gttttacgat ttaactttcc gagtagtgtc   480
acgtttgaca tgggagttta cgaggaactt tcaactgcag taatgagaat agttgatagg   540
tttgtatga                                                           549

SEQ ID NO: 2           moltype = DNA  length = 18
FEATURE                Location/Qualifiers
source                 1..18
                       mol_type = other DNA
                       organism = synthetic construct
SEQUENCE: 2
aacacggggg actctaga                                                  18

SEQ ID NO: 3           moltype = DNA  length = 21
FEATURE                Location/Qualifiers
source                 1..21
                       mol_type = other DNA
                       organism = synthetic construct
SEQUENCE: 3
tacaaaccta tcaactattc t                                              21

SEQ ID NO: 4           moltype = DNA  length = 25
FEATURE                Location/Qualifiers
source                 1..25
                       mol_type = other DNA
                       organism = synthetic construct
SEQUENCE: 4
caccatggga attctcttgc ctcct                                          25

SEQ ID NO: 5           moltype = DNA  length = 22
FEATURE                Location/Qualifiers
source                 1..22
                       mol_type = other DNA
                       organism = synthetic construct
SEQUENCE: 5
tacaaaacct atcaactatt ct                                             22

SEQ ID NO: 6           moltype = DNA  length = 20
FEATURE                Location/Qualifiers
source                 1..20
                       mol_type = other DNA
                       organism = synthetic construct
SEQUENCE: 6
cccgaaacct gcataaaatg                                                20
```

```
SEQ ID NO: 7            moltype = DNA  length = 20
FEATURE                 Location/Qualifiers
source                  1..20
                        mol_type = other DNA
                        organism = synthetic construct
SEQUENCE: 7
gcgatcaaat tggttttcgt                                                    20
```

PECTIN METHYLESTERASE INHIBITOR GENE GhPMEI39 AND APPLICATION OF ITS ENCODED PROTEIN

REFERENCE TO AN ELECTRONIC SEQUENCE LISTING

The content of the electronic sequence listing (filename: 2024-04-18_SequenceListing.xml; Size: 7787 bytes; and Date of Creation: Apr. 18, 2024) is herein incorporated by reference in its entirety.

TECHNICAL FIELD

The present disclosure relates to the field of regulation of plant performance genes, in particular to a pectin methylesterase inhibitor gene GhPMEI39 and application of its encoded protein.

BACKGROUND

A vascular bundle is an important transportation channel for plants, mainly includes phloem cells and xylem cells, and is responsible for transporting water, inorganic salts, organic substances, various proteins, amino acids, etc. during plant development, thereby regulating the vegetative growth and the reproductive growth of plants. Previous studies have shown that CLE25, APL and other genes play an important role in regulating the initiation and development of phloems of plants. PMEI is a cell wall pectin methylesterase inhibitor, which plays an important role in regulating the toughness, permeability and biochemical properties of a cell wall, thereby affecting seed germination, pathogen invasion and other plant development and interaction with external factors.

HG is the most abundant pectin polymer, and HG methyl esterification has a significant effect on the rheological properties of cell walls and plant development. Demethylated HG can be easily hydrolyzed by pectin-degrading enzymes, such as endogalacturonase, or form rigid gels by promoting the formation of intermolecular calcium bonds and a so-called egg-box model structure, which means that demethylated HG has a dual role. In addition, HG methyl esterification can also hinder the establishment of calcium bridges and increase the flexibility of cell walls. The degree of HG methyl esterification (DM) is thought to be mediated through the transfer and release of methyl groups through the counteraction of pectin methyltransferase (PME) and PME/invertase inhibitor (PMEI), which form a large family of plant sequences, named PMEI-related proteins (PMEI-RPs) that interact directly through an integral hairpin motif.

Flowering is an important trait of plants, which is related to the yield of crops and the economic value of ornamental plants, but its specific regulatory mechanism is still unclear.

In view of this, the present disclosure is proposed.

SUMMARY

Existing studies have proved that pectin methylesterase mainly affects plant disease resistance, such as bacterial or fungal diseases. According to the present disclosure, a gene cloning technology and a plant transgene are used to verify the effect of a cotton pectin methylesterase inhibitor gene GhPMEI39 and its encoded protein in plants.

Based on the above contents, the present disclosure provides the following technical solutions:

The present disclosure provides a pectin methylesterase inhibitor gene GhPMEI39, whose gene sequence is shown in SEQ ID NO: 1.

The present disclosure provides the pectin methylesterase inhibitor gene GhPMEI39, which is cloned from cotton by a biological means.

According to the present disclosure, a public database is used to screen target genes, primers are designed to clone the target genes, its cotton transgenic materials and *Arabidopsis thaliana* transgenic materials are constructed, plant development phenotypes after overexpression and constitutive expression of the pectin methylesterase inhibitory protein are analyzed, and the role of the pectin methylesterase inhibitor gene GhPMEI39 in related functions such as plant flowering and inflorescence morphology is verified.

Specifically, the present disclosure further provides application of the pectin methylesterase inhibitor gene GhPMEI39 or its homologue or encoded protein in regulating any one or more of the following properties of plants:
  (a) differentiation of vascular tissues;
  (b) development of the vascular tissues;
  (c) differentiation of inflorescences;
  (d) development of the inflorescences; and
  (e) differentiation of flower buds; The gene sequence of the pectin methylesterase inhibitor gene GhPMEI39 is shown in SEQ ID NO:1.

Further, the differentiation of vascular tissues of plants includes the number of vascular tissues.

The development of the vascular tissues includes the number of cells in a phloem and a xylem of a vascular bundle.

The differentiation of inflorescences includes the number of inflorescences.

The development of the inflorescences includes the number of cells in vascular tissues of the inflorescences.

The differentiation of flower buds includes the number of flower buds.

Further, the vascular tissues include the vascular tissues in stem and leaf organs.

Experiments show that the pectin methylesterase inhibitor gene GhPMEI39 provided by the present disclosure can affect the number of vascular tissues and change the number of cells in the phloem and the xylem of the vascular bundle in terms of the vascular tissues, can affect the number of inflorescences and change the number of cells in the vascular tissues of the inflorescences in terms of inflorescences, and can change the number of flower buds in terms of flower buds.

The stem includes a primary stem and a first rosette leaf.

Specially, the plant is cotton, and the overexpression of the pectin methylesterase inhibitor gene GhPMEI39 promotes the development of stems of fruit branches of cotton and increases the number of flower buds.

If the plant is an economic crop similar to cotton and the like, the overexpression of the pectin methylesterase inhibitor gene GhPMEI39 can promote the development of the stems of fruit branches of cotton and increase the number of flower buds, thereby achieving the effect of increasing the yield of the cotton.

It should be noted that the cotton in the present disclosure may be various planting cotton, such as upland cotton (*Gossypium hirsutum*), sea island cotton (*Gossypium barbadense*), Asian cotton (*Gossypium arboreum*) and grass cotton (*Gossypium herbaceum*) and the variants of these cotton varieties. That is to say, the cotton varieties with the same or similar genes as the gene GhPMEI39 of the present disclosure are also within the protection scope of the present disclosure. For example, the sequence similarity between the similar gene and the gene GhPMEI39 of the present disclosure may reach more than 80%, or more than 85%, or more than 90%, or more than 95%, or more than 96%, or more than 97%, or more than 98%, or more than 99%, etc.

The plant is *Arabidopsis thaliana*, and the overexpression of the pectin methylesterase inhibitor gene GhPMEI39 increases the number of *Arabidopsis thaliana* inflorescences, increases the transverse diameters of main stems and rosette leaves, and increases the number of flower buds.

Further, the plant is *Arabidopsis thaliana*, and the overexpression of the pectin methylesterase inhibitor gene GhPMEI39 increases the number of cells in the phloem in the first rosette leaf, increases the number of vascular tissues in the primary stem, and increases the number of phloems in a single vascular tissue.

If the plant is *Arabidopsis thaliana* and other similar cruciferous plants, the thickness of stems and leaves of *Arabidopsis thaliana* may be improved by overexpressing the pectin methylesterase inhibitor gene GhPMEI39, the number of inflorescences and flower buds may be increased, and the yield of the plants may be increased.

The application of the pectin methylesterase inhibitor gene GhPMEI39 provided by the present disclosure is not limited to the above plants, and may also be used in the regulation of inflorescence traits of other plants such as ornamental plants and the regulation of wood hardness of woody plants.

Further, the plants include cruciferous plants, ornamental plants, economic crops, and woody plants.

Further, the cruciferous plants include *Arabidopsis thaliana*, radish, rape, and cabbage.

The ornamental plants include *chrysanthemum*, rose, Chinese rose, and violet.

The economic crops include cotton, oilseeds, sugar crops, tobacco leaves, hemp, and alfalfa.

The woody plants include poplar, pine, and cypress.

In the present disclosure, when the pectin methylesterase inhibitor gene GhPMEI39 is applied to different plants, the gene sequence used may be the pectin methylesterase inhibitor gene GhPMEI39 or its homologue, and the homolog includes not only pectin methylesterase inhibitor genes in different plants, but also pectin methylesterase inhibitor genes in own plants. Generally, the sequence similarity of homologous genes is more than 80%, for example, in different plants, the similarity may be more than 85% or 90%, or 95%, or 96%, or 97%, or 98%, or 99%, etc.

The present disclosure further provides a method for detecting cotton varieties. The method comprises the following steps: detecting whether a sample to be tested contains the overexpressed pectin methylesterase inhibitor gene GhPMEI39 or a product produced by the overexpressed pectin methylesterase inhibitor gene GhPMEI39 or not; and if so, judging that the sample to be tested has higher cotton yield performance, where the gene sequence of the pectin methylesterase inhibitor gene GhPMEI39 is shown in SEQ ID NO:1.

Because the overexpressed pectin methylesterase inhibitor gene GhPMEI39 plays a role in increasing the yield of the cotton as described above, in different cotton varieties or in breeding, if a plant containing the overexpressed pectin methylesterase inhibitor gene GhPMEI39 is selected, it is necessary to detect whether the sample to be tested contains the overexpressed pectin methylesterase inhibitor gene GhPMEI39 or not. The detection is not limited to the pectin methylesterase inhibitor gene GhPMEI39, and a marker for overexpression, an overexpressed product, etc., may also be detected. The detection of the product produced by the pectin methylesterase inhibitor gene GhPMEI39 may be performed by various means, such as an ELISA detection kit.

Further, a primer pair or a probe or a chip designed by overexpressing an element of the pectin methylesterase inhibitor gene GhPMEI39 is used to detect the sample to be tested.

Further, the nucleic acid sequences of the primer pair are shown in SEQ ID NO. 2 and SEQ ID NO. 3.

Further, the sample to be tested includes materials suitable for tissue culture of sexually reproducing cells, asexually reproducing cells or regenerable cells.

Materials suitable for sexually reproducing is, for example, selected from pollen, ovary, ovule, embryo sac, etc.

Materials suitable for asexually reproducing, for example, may be selected from cuttings, roots, stems, protoplasts, etc.

Materials suitable for tissue culture of regenerable cells, for example, may be selected from leaves, pollen, embryos, cotyledons, hypocotyls, meristematic cells, roots, root apices, anthers, flowers, seeds, stems, etc.

Further, the sample to be tested includes any one of the following materials: seeds, leaves, roots, stems, radicles, and germs.

The present disclosure further provides a breeding method for increasing the yield of cotton. The breeding method includes the following steps: recombining a fragment containing the overexpressed pectin methylesterase inhibitor gene into a cotton genome; and screening to obtain the plants containing the element of the overexpressed pectin methylesterase inhibitor gene.

The gene sequence of the pectin methylesterase inhibitor gene GhPMEI39 is shown in SEQ ID NO:1.

According to the present disclosure, the target fragment is recombined into the cotton genome, and this process will involve some means of transformation, such as a common *Agrobacterium tumefaciens* mediated method, a gene gun method, a PEG method, a laser microbeam puncture method, a microinjection method, a pollen-mediated method, etc. These methods can be accomplished according to technical steps in the art.

The plants containing the overexpressed element of the pectin methylesterase inhibitor gene GhPMEI39t are obtained through screening, and the plants at this place may represent the reproductive material of the plant, and may also be the non-reproductive material of the plant, that is, a part of the material of the plant itself after gene transformation, these materials include, but are not limited to, tubers, branches, roots, protoplasts, leaves, embryos, cotyledons, hypocotyls, meristematic cells, root apices, anthers, flowers, seeds, pollen, ovaries, ovules, and embryo sacs.

Screening to obtain the plant containing the overexpressed pectin methylesterase inhibitor gene GhPMEI39 can be achieved by various means, such as molecular biological means, including, but not limited to, detecting the sample to tested by the primer pair or probe or chip of the pectin methylesterase inhibitor gene GhPMEI39.

If the product produced by the overexpressed pectin methylesterase inhibitor gene GhPMEI39 is detected, some expression-visible markers may be set on an overexpression vector, for example, may be detected by ELISA detection kits, or may be marked through displaying by fluorescence in specific cases.

The pectin methylesterase inhibitor gene GhPMEI39 of the present disclosure is used to assist high-quality performance breeding of cotton fibers, so that target cotton may be screened out at an early stage, and the time is reduced.

Compared with the prior art, the present disclosure at least has the following beneficial effects:

(1) The present disclosure provides the pectin methylesterase inhibitor gene GhPMEI39, the public database is used to screen the target genes, and primers are designed to clone the target genes.

(2) By constructing its cotton transgenic materials and *Arabidopsis thaliana* transgenic materials, and analyzing the plant development phenotypes after overexpression and constitutive expression of the pectin methylesterase inhibitory protein, it was first discovered the role of the pectin methylesterase inhibitor gene GhPMEI39 in plant flowering, inflorescence morphology and other related functions.

(3) The pectin methylesterase inhibitor gene GhPMEI39 provided according to the present disclosure may be applied to yield increase of various plants such as economic crop cotton and other similar crops, and may also be used in the regulation of inflorescence traits of other plants such as ornamental plants and the regulation of wood hardness of woody plants.

(4) The pectin methylesterase inhibitor gene GhPMEI39 provided according to the present disclosure is expected to find genes with similar functions in other plants, which will provide good technical support for further research.

BRIEF DESCRIPTION OF DRAWINGS

In order to more clearly illustrate the examples of the present disclosure or the technical solutions in the prior art, the following will briefly introduce the drawings that need to be used in the description of the examples or the prior art.

DETAILED DESCRIPTION

Examples of the present disclosure will be described in detail below in conjunction with examples, but those skilled in the art will understand that the following examples are only for illustrating the present disclosure, and should not be considered as limiting the scope of the present disclosure. Those who do not indicate the specific conditions in the examples are carried out according to the conventional conditions or the conditions suggested by the manufacturer.

The reagents or instruments used are conventional products that can be purchased from the market if the manufacturer is not indicated.

Example 1

1. Cloning of the Cotton Pectin Methylesterase Inhibitor Gene (GhPMEI39)

GhPMEI39 cDNA is based on the total cDNA of cotton 5DPA ovules of 24 (ZM24) of Institute of Cotton Research of CAAS as a template, and 5'-CACCATGGGAAT-TCTCTTGCCTCCT-3'(sense) (SEQ ID NO:4) and 5'-TA-CAAAACCTATCAACTATTCT-3'(antisense) (SEQ ID NO:5) as primers for PCR amplification to obtain a 553 bp gene sequence (as shown in SEQ ID NO: 1). The entry clone of pENTR-GhPMEI39 was constructed by a gateway and verified by sequencing.

2. Expression, Purification and Enzyme Activity Verification of GhPMEI39 Protein in *Escherichia coli*

(1) Prokaryotic Induction and Purification of GhPMEI39 Protein

An Infusion technology and a pColdTF expression vector were used to amplify the GhPMEI39-specific PCR product so that the 5' and 3' ends have the same sequence as the two ends of a linearized vector (BamHI/ECORI double enzyme digestion linearization), respectively. The pColdTF-GhP-MEI39 recombinant plasmid was obtained by a seamless cloning method with reference to an Ultra One Step Cloning Kit (Vazyme, Cat. #115-02) and contained a 6× His-Tag. The pColdTF-GhPMEI39 recombinant plasmid was transformed into *Escherichia coli* BL21 (DE3) competent cells. Transformed cells were activated and cultured in Luria-Bertani (LB) medium containing 50 µg/ml ampicillin. When the cell density reached 0.4-0.6 optical density at 600 nm (OD600), isopropyl-1-thio-propanediol-D-galactoside (IPTG) was added to the LB medium at a final concentration of 0.5 mM. After culturing overnight at 16° C., the cells were centrifuged at 5000 g for 10 min at 4° C., and the pelleted cells were resuspended in a binding buffer (50 mM Tris-HCl, 150 mM NaCl, pH 7.5). The suspension was sonicated, and the lysate was centrifuged at 12000 g for 10 min at 4° C. Referring to a Ni Sepharose™6 Fast Flow (GE Healthcare; Cat. #11-0008-87) purification method, the supernatant was applied to the his-binding column with nickel, the target protein was eluted with the elution buffers containing 30 mM, 50 mM and 100 mM imidazole, respectively, after the column penetrating liquid was collected, and the eluate was collected. An SDS-PAGE detection purification effect is shown in FIG. 1.

Figure 1:
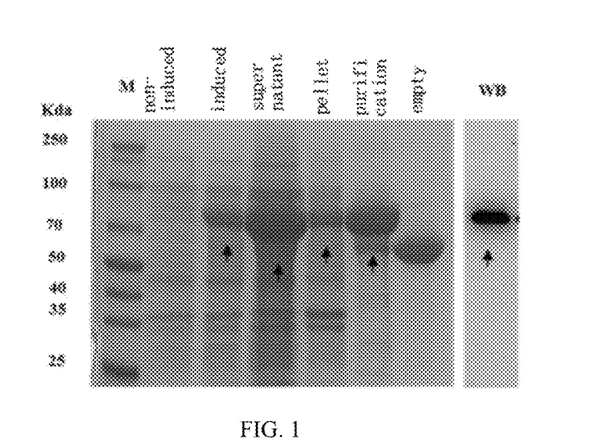
FIG. 1 is an electrophoresis diagram of a recombinant GhPMEI39 protein expressed in *Escherichia coli* BL21 (DE3) through SDS-PAGE analysis according to the example 1 of the present disclosure.

In FIG. 1, M is a protein marker; non-induced represents the cell lysate of pColdTF-GhPMEI39 transformed bacteria before IPTG induction; induced represents the cell lysate of pColdTF-GhPMEI39 transformed bacteria under IPTG induction; the supernatant represents the supernatant of the cell lysate of pColdTF-GhPMEI39 transformed bacteria under IPTG induction; pellet represents the pellet of the cell lysate of pColdTF-GhPMEI39 transformed bacteria under IPTG induction; purification shows purified GhPMEI39 protein; empty shows purified pColdTF empty protein; WB shows Western blot analysis of purified GhPMEI39 protein using GhPMEI39 autoantibody; and the bands indicated by the arrows represent GhPMEI39 fusion protein under IPTG induction.

(2) Enzyme Activity Detection

Figure 2:
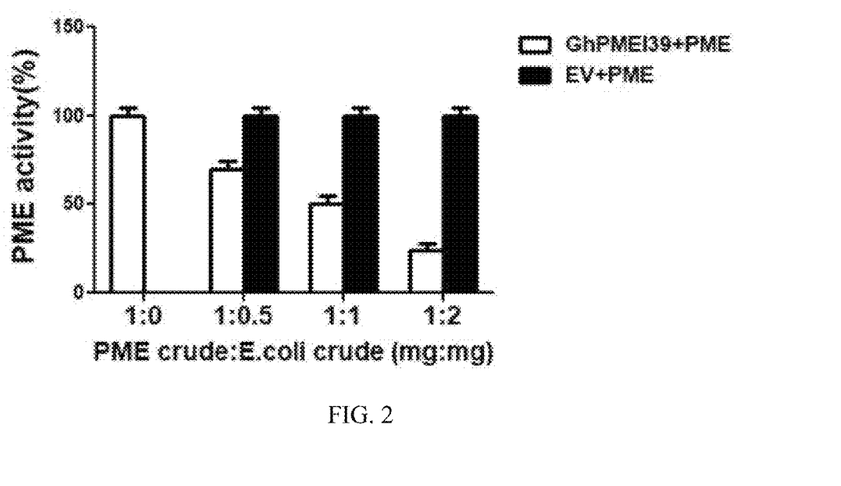
FIG. 2 is a bar graph of an in vitro inhibitory activity of a GhPMEI39 protein to a PME crude extract of an *Arabidopsis thaliana* stem according to Example 1 of the present disclosure.

On this basis, the inhibitory activity of GhPMEI39 protein on the PME was further determined. The method is as follows: to obtain a PME crude extract, a 1 g of *Arabidopsis thaliana* stem (1 month old) tissue was ground with liquid nitrogen and then dissolved in 1 ml of extraction buffer (PBS pH 7.4, 1 M NaCl) to form a homogenate, after standing on ice for 1 h (inverted upside down and mixed for 3 times), the homogenate was centrifuged at 11000 g for 10 min, which is repeated once, and the supernatant was collected and stored in ice. Protein concentration was measured with a NanoDrop2000 spectrophotometer (Thermo Science, USA). A PMEI purified protein and the PME crude extract were placed in a water bath at 25° C. for 30 min before the enzyme activity assay. A reaction solution mixture added to each reaction tube includes 1 ml 0.5% (w/v) pectin, 400 μl 0.01% bromothymol blue, 1.50 ml distilled water (mixture pH=7.5), followed by addition of 100 μl mixture with different proportions of PME:GhPMEI3 of (1:0, 1:0.5, 1:1 and 1:2), the mixtures were incubated at 30° C. for 16 h, the OD value of the reactant at a wavelength of 620 nm was detected, and the ΔOD value of the reactant with different proportions of PME:PMEI within 1 s was calculated. In this experiment, a pColdTF empty induced protein was used as the impression control. The results are shown in FIG. 2. With the ratio of PME:GhPMEI39 changing from 1:0 to 1:2, the PME enzyme activity in the corresponding reaction solution also decreased from 100% to 24%, while the PME enzyme activity in the reaction solution did not change after the negative control pColdTF empty induced protein was added, indicating that GhPMEI39 protein has the ability to inhibit the PME activity.

In FIG. 2, the crude protein of pColdTF-GhPMEI39 or an empty vector (pColdTF–, EV) was extracted from *Escherichia coli* BL21 cells expressing pColdTF-GhPMEI39 or empty vector (up to pColdTF, EV) after IPTG induction. Error bars represent S.E.M. (n≥3). 1:0, 1:0.5, 1:1, 1:2 represent the ratio of the PME crude extract from *Arabidopsis thaliana* stem to pColdTF-GhPMEI39 or empty vector pColdTF crude extract protein in *Escherichia coli* BL21, where the white column represents PME: pColdTF—GhPMEI39 reaction solution, and the black column represents PME: pColdTF—empty reaction solution.

3. Analysis of Subcellular Localization of GhPMEI39 Protein

Figure 3:
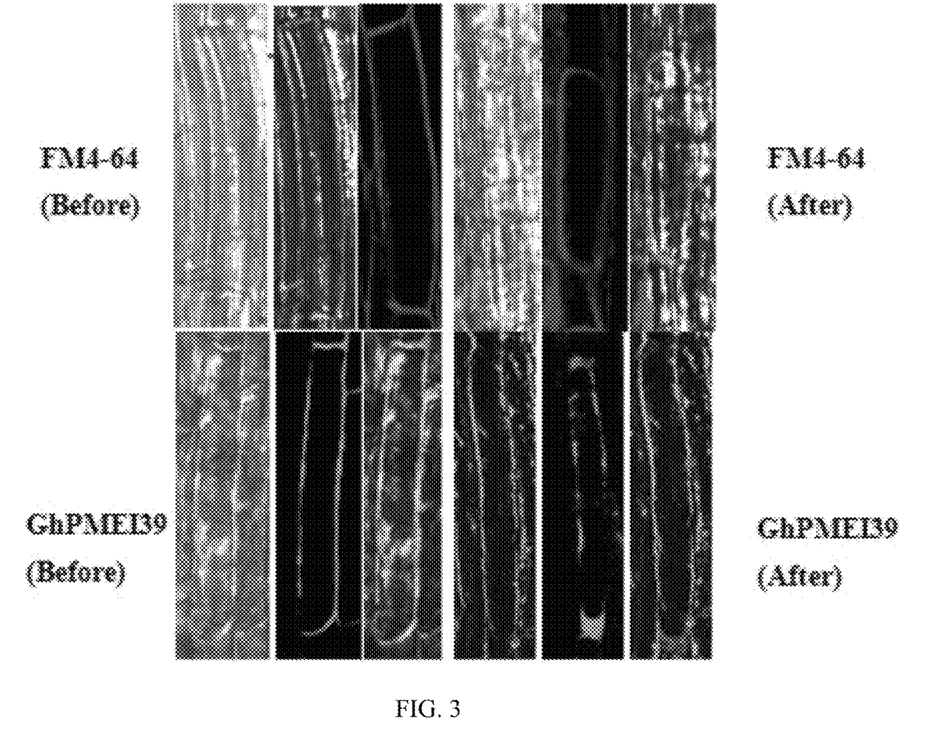
FIG. 3 is a subcellular localization map of a GhPMEI39 protein according to the embodiment of the present disclosure 1.

Vector pCAMBIA2300: The construction of GhPMEI39:YFP, the GhPMEI39 CDS PCR product was cloned into the upstream of a Kpn1/Asc1YFP (yellow fluorescent protein) gene to produce a GhPMEI39:YFP fusion protein, and the GhPMEI39:YFP fusion protein was transformed into GV3101 *Agrobacterium tumefaciens*, and the 35S:GhPMI39:YFP overexpression transgenic *Arabidopsis thaliana* was obtained by a Floral-dip method. The positive seedlings of *Arabidopsis thaliana* grown for 4 days and the roots of WT were used as observation objects, and were observed by an LSM 510 laser confocal scanning microscope. The green (YFP) was the localization of a GhPMEI39 protein, and the red (FM4-64, cell membrane dye) fluorescent marker was a cell membrane (FIG. 3). To determine the specific localization of a GhPMEI39:YFP cell wall or a cell membrane, the seedling roots were treated with 0.4 M NaCl for 20 min and then observed. The results of the study are shown in the Figure below. The GhPMEI39 protein is located between the cell wall and the cell membrane and is an exocrine protein.

In FIG. 3, Before represents the localization before the seedlings treated with 0.4 M NaCl, and After represents the localization after the plasmolysis of the roots of the seedlings treated with 0.4 M NaCl.

Example 2

1. Construction of GhPMEI39 Transgenic *Arabidopsis Thaliana* Vector

Using pENTR-GhPMEI39 and Gateway LR reactions, the GhPMEI39 cDNA fragment was cloned into a target vector PGWB2 (CaMV 35S promoter). The pGWB2-GhPMEI39 Ti plasmid was transformed into the *Agrobacterium tumefaciens* strain GV3101 to obtain 35S:GhPMEI39 overexpression transgenic *Arabidopsis thaliana* by a Floral-dip method.

2. DNA Extraction and GhPMEI39 Expression Detection

A total of 12 quasi-overexpressed transgenic GhPMEI39 *Arabidopsis thaliana* plants were obtained, DNA from 10 quasi-transgenic plants and WT plants was extracted, and CaMV35S5'-AACACGGGGGACTCTAGA-3'(sense) (SEQ ID NO:2) and GhPMEI395'-TACAAACCTATCAAC-TATTCT-3'(antisense) (SEQ ID NO:3) were used as primers to amplify and detect DNA, and 12 overexpressed transgenic GhPMEI39 *Arabidopsis thaliana* plants were banded (FIG. 4A). By detecting the expression of GhPMEI39 in 9 *Arabidopsis thaliana* stems, it was found that compared with the negative control WT, the expression of 6 transgenic plants were all up-regulated (FIGS. 4B, 4C).

Figure 4:
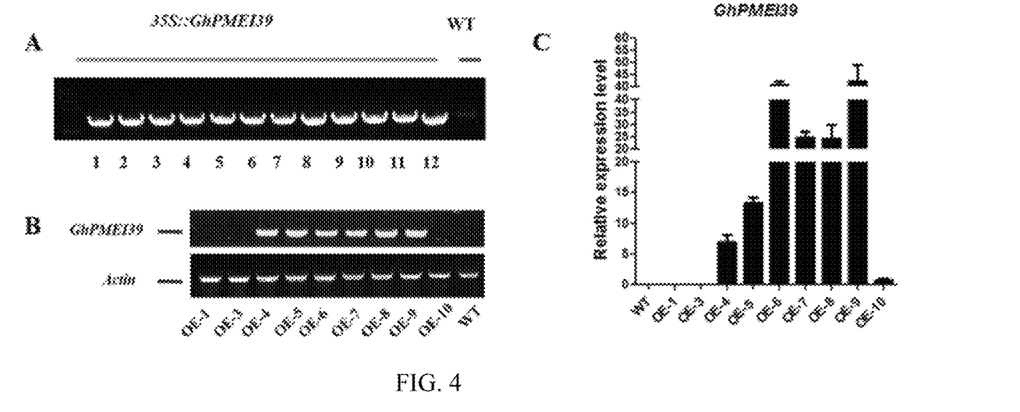
FIG. 4 is a gene identification and expression diagram of an *Arabidopsis thaliana* plant overexpressed with GhPMEI39 according to Example 2 of the present disclosure.

In FIG. 4, A represents the DNA identification map of 12 GhPMEI39 transgenic *Arabidopsis thaliana*, B and C are semi-quantitative and qRT-PCR identification results of the RNA expression level of GhPMEI39 transgenic *Arabidopsis thaliana* plants, and the Bar value represents a standard difference of three repeated PCRs.

3. Phenotype Observation of GhPMEI39 Transgenic *Arabidopsis Thaliana*

Figure 5:
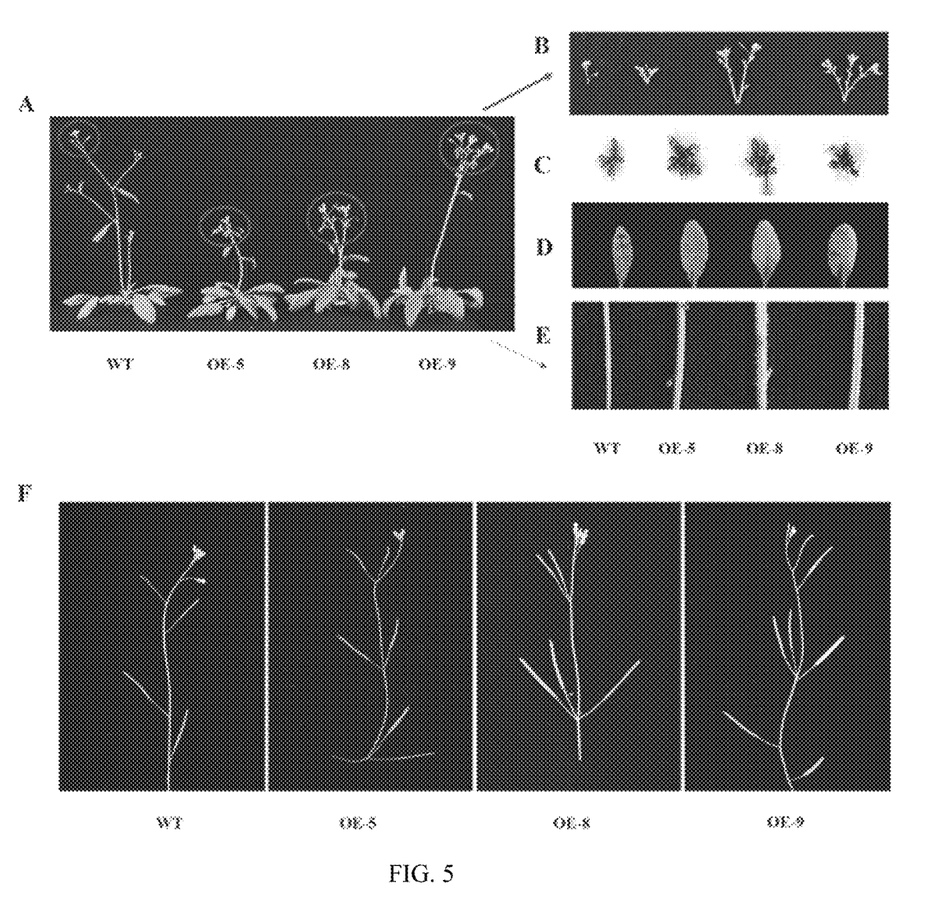
FIG. 5 is a phenotype diagram of an *Arabidopsis thaliana* plant overexpressed with GhPMEI39 according to Example 2 of the present disclosure.

Further, single-copy homozygotes were obtained by selecting three lines of GhPMEI39-5, 8, 9 for phenotype observation, and the results are shown in FIG. 5. In FIG. 5, A represents the phenotype diagram of *Arabidopsis thaliana* of three transgenic lines of GhPMEI39OE-5, 8, 9 and WT plants, and B, C, D, and E represent the diagrams of the primary inflorescence, flower bud, and first rosette leaf and main stem of GhPMEI39 transgenic *Arabidopsis thaliana* and WT plants, respectively. F is the diagram of the main stems and fruit pods of *Arabidopsis thaliana* of three transgenic lines of GhPMEI39OE-5, 8, 9 and WT plants.

Through the observation of the three transgenic lines and WT plants, it was found that the transverse diameters of the main stems and rosette leaves of the three transgenic plants OE-5, 8, 9 overexpressing GhPMEI39 were increased (FIGS. 5A, 5D, 5E), More importantly, due to the overexpression of the GhPMEI39 gene, the primary main stem inflorescence of *Arabidopsis thaliana* changed from one to two or three in the wild type, and the number of flower buds also increased significantly (FIG. 5A-5C), resulting in the phenotype of two or even three fruit pods at the same time at one fruit pod growing point on the main stem (FIG. 5F).

4. The Overexpression of GhPMEI39 Increased the Number of Vascular Tissue Cells in the First Rosette Leaf and Primary Stem of *Arabidopsis Thaliana*.

Figure 6:
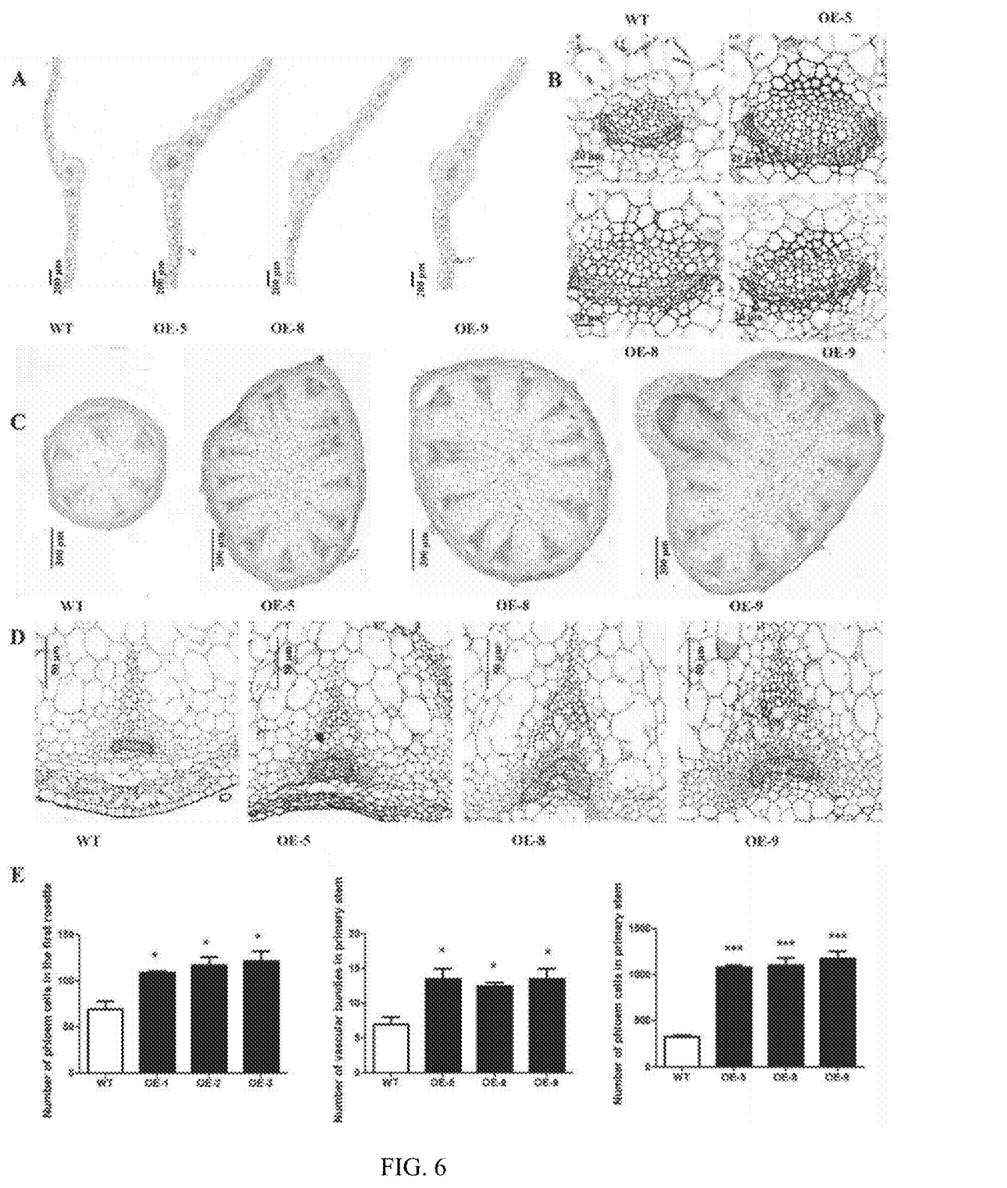
FIG. 6 is a correlation diagram of a first rosette leaf and a phloem of a main stem of *Arabidopsis thaliana* overexpressed with GhPMEI39 according to Example 2 of the present disclosure.

In order to explore the reasons for the increase in the transverse diameters of leaves and main stems of the three transgenic lines of GhPMEI39 and WT plants, the vascular tissue structures of the main stems and rosette leaves of the three transgenic lines OE-5, 8, 9 overexpressing GhPMEI39 were further observed by paraffin section, and the results are shown in FIG. 6. In FIG. 6, A represents the transverse cut of the vein of the first rosette leaf of *Arabidopsis thaliana* of three transgenic lines of GhPMEI39OE-5, 8, 9 and the WT plants, B is an enlarged view of the vascular tissue in FIG. A, C is a structure diagram of vascular tissues of the main stems of WT and OE lines, D is a method diagram of a single vascular tissue in FIG. C, E is the number of phloem cells in the first rosette leaves, the total number of vascular tissues in the primary inflorescence and the total number of phloems in GhPMEI39 transgenic *Arabidopsis thaliana* and wild plants, where n=6.

Due to the overexpression of GhPMEI39, the number of phloem cells in the first rosette leaf increased from 69 in WT to 108, 117, 121 in OE lines (FIG. 6A, 6B, 6E), while the number of vascular tissues in the primary stem also increased from 6-8 in WT to 12-15 in OE transgenic materials. The number of phloem cells in single vascular tissue also increased significantly, resulting in a significant increase in the number of phloem cells throughout the primary stem from 330 in WT to 1079-1181 (FIGS. 6C, 6D, 6E).

5. GhPMEI39 Overexpression Increases the Degree of Methylation (DM) in Primary Stems of *Arabidopsis Thaliana*

Figure 7:
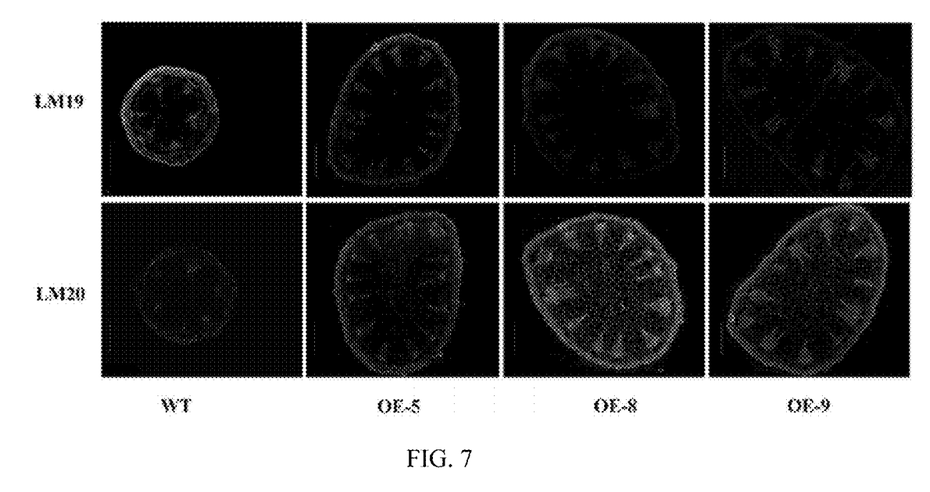
FIG. 7 is an immunolocalization map of pectin in a vascular tissue of a cross section of a primary stem of *Arabidopsis thaliana* according to Example 2 of the present disclosure.

Through the immunological observation of the vascular tissue cross-sections of the primary stems of three OE lines and WT *Arabidopsis thaliana* plants with two pectin antibodies LM19 and LM20 representing different degrees of methylation, it was found that in the OE line, LM19, which is the indicator of low methylation pectin, has a weak fluorescence, and LM20, which is the indicator of high methylation pectin, has a strong fluorescence, while WT shows the opposite trend (FIG. 7). In FIG. 7, LM19 represents low methylation pectin, while LM20 represents high methylation pectin, and Bar=300 μm for all images.

The results showed that the methylated pectin content was higher in the OE line, that is, GhPMEI39 overexpression increases the degree of methylation (DM) in primary stems of *Arabidopsis thaliana*.

Example 3

1. Construction of GhPMEI39 Transgenic Cotton

Using pENTR-GhPMEI39 and Gateway LR reactions, the GhPMEI39 cDNA fragment was cloned into the target vector PGWB2 (CaMV35S promoter). The pGWB2-GhPMEI39Ti plasmid was transformed into *Agrobacterium tumefaciens* strain LBA4404, and the hypocotyls of 7-day-old ZM24 sterile cotton seedlings (5 days in the dark and 2 days in the light) were used as explants for dip-dyeing cultivation to obtain transgenic overexpressed cotton.

2. DNA Extraction and GhPMEI39 Expression Detection

Plant Genomic DNA extraction Kit (BioTeke, Cat #DP3112) was used to extract the genomic DNA from all the quasi-transgenic plants obtained through tissue culture and from the tender leaves of ZM24 cotton, using DNA as a template, CaMV35S-F: 5'-AACACGGGGGACTCTAGA-3'(sense) (SEQ ID NO:2) and GhPMEI39-R:5'-TACAAACCTATCAACTATTCT-3'(antisense) (SEQ ID NO:3) were used as primers for PCR amplification, and the expression of the plants with 562 bp fragment was further detected by gel detection.

In order to determine the expression level of GhPMEI39 in transgenic and wild cotton plants, 5DPA ovules of transgenic GhPMEI39 and wild ZM24 cotton were collected at 8:00 to 9:00, soaked in liquid nitrogen and stored in a −80° C. refrigerator, or RNA was isolated from all samples after immediate trituration according to the instructions of the polysaccharide polyphenol plant total RNA extraction kit (Tiangen, Cat. #DP441). About 1 μg of total RNA was reverse-transcribed using reverse transcriptase (Invitrogen, Cat. #18080-093) to obtain cDNA. For qRT-PCR, GhUBQ7 (DQ116441) was used as an internal reference gene, and the primers were as follows: 5'-CCCGAAACCTGCAT-AAAATG-3'(sense) (SEQ ID NO:6) and 5'-GCGAT-CAAATTGGTTTTCGT-3'(antisense) (SEQ ID NO:7).

The 5DPA ovules of transgenic and wild cotton stored at −80° C. were taken out, ground into powder in liquid nitrogen, and then protein extract (150 mM NaCl; 1 M Tris-HCl, pH=7.5; 0.1% NP40; 0.1% Triton X-100) was added. After mixing well, standing on ice is performed for 30 mins, followed by centrifuging at high speed at 12000 g at 4° C. for 10 min, and the supernatant is taken. A GhPMEI39 polyclonal antibody was produced by Shanghai Youke Biotechnology Co. Ltd. Western blotting experiments were performed according to previous reports.

Figure 8:
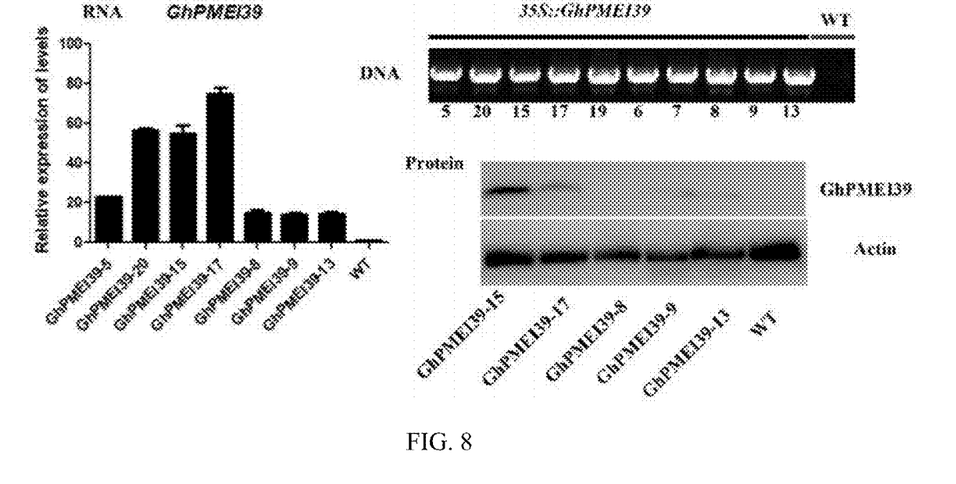
FIG. 8 is a correlation diagram for an identification of overexpressed transgenic cotton according to Example 3 of the present disclosure.

A total of 146 quasi-overexpressed transgenic GhPMEI39 cotton plants were obtained, DNA from all quasi-transgenic plants and WT plants was extracted, and CaMV35S5'-AACACGGGGGACTCTAGA-3'(sense) (SEQ ID NO:2) and GhPMEI395R:5'-TACAAACCTATCAACTATTCT-3' (antisense) (SEQ ID NO:3) were used as primers to amplify and detect DNA, as shown in the DNA of FIG. 8, and a total of 10 overexpressed transgenic GhPMEI39 cotton lines were banded.

By detecting the expression of GhPMEI39 in the 5DPA ovules of 7 plants, it was found that (RNA in FIG. 8), compared with the negative control WT, the expressions in all transgenic plants were up-regulated, and five lines with low, medium and high expressions of GhPMEI39—8, 9, 13, 15, 17 were randomly selected. Western blot detection with GhPMEI39 autoprotein antibody revealed that compared with WT, the protein levels of GhPMEI39—9, 13, 15, 17 in the four lines were also up-regulated (Protein in FIG. 8), indicating that the four lines were indeed transgenic GhPMEI39 overexpression plants.

3. Phenotype Analysis of Transgenic Plants

By observing the vegetative growth and reproductive growth stages of three transgenic lines and ZM24 plants, it was found that the vegetative growth of transgenic plants OE-13, 15, 17 overexpressing GhPMEI39 had no difference compared with ZM24, but at the reproductive growth stage, overexpression of GhPMEI39 promoted the appearance of a flower bud cluster phenotype in fruit branches (FIG. 9A, 9B), and the flower bud cluster may further develop into flowers and even mature cotton bolls (FIG. 9C). At the same time, by observing the stem structures of fruit branches of the three OE lines and ZM24, it was found that the overexpression of GhPMEI3 may promote the development of phloem in the stems of the fruit branches (FIG. 9D).

Figure 9:
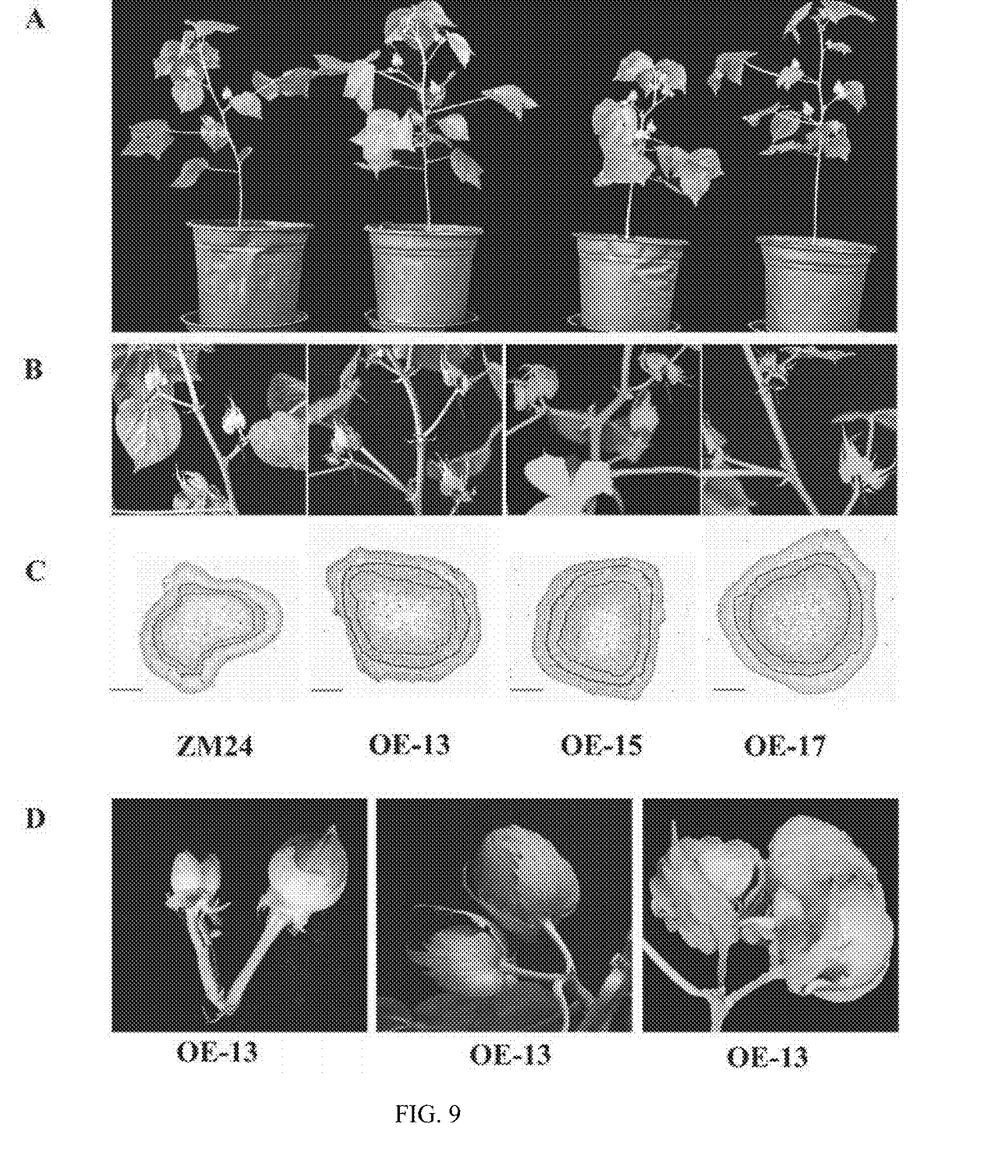
FIG. 9 is an observation diagram of a reproductive growth phenotype of transgenic cotton overexpressing GhPMEI39 according to Example 3 of the present disclosure.

In FIG. 9, A shows whole plant phenotypes of ZM24 and transgenic cotton lines OE-13, 15, and 17 overpressing GhPMEI39 from left to right at the budding stage. FIG. B is an enlarged view of flower bud differentiation of different lines in FIG. A. FIG. C is an observation of the vascular tissue structures in the stems of the fruit branches of the ZM24 and OE lines, where bar=600 μm. FIG. D is the string bolls and mature fibers formed by the transgenic line OE-13.

Summarizing the above studies, it was found that the overexpression of GhPMEI39 promoted the development of plant vascular tissues, especially the phloem, thereby changing the inflorescence differentiation and inflorescence characteristics.

The DPA is the abbreviation of days post anthesis, which means the number of days after flowering.

While the present disclosure has been illustrated and described with special embodiments, it should be appreciated that various other changes and modifications can be made without departing from the spirit and scope of the present disclosure. Therefore, this means that all such changes and modifications that fall within the scope of the present disclosure are included in the appended claims.

The invention claimed is:

1. A method of increasing development of vascular tissue and/or inflorescences of a dicot plant, comprising
   (a) overexpressing a *Gossypium hirsutum* methylesterase inhibitor 39 (GhPMEI39) gene within the dicot plant, wherein the GhPMEI39 gene comprises the sequence SEQ. ID. NO: 1; and
   (b) selecting a dicot plant from (a) for having an increased number of cells in the phloem of a vascular bundle, for having an increased number of cells in the xylem of a vascular bundle, and/or for having an increased number of cells in a vascular tissue of the inflorescences,
   wherein the dicot plant is *Gossypium hirsutum* and the dicot plant from (a) is selected for having increased development of a fruit branch stem or for having an increased number of flower buds; or
   the dicot plant is *Arabidopsis thaliana* and the dicot plant from (a) is selected for having an increased number of inflorescences, for having an increased transverse diameter of its main stem, for having an increased transverse diameter of a rosette leaf, or for having an increased number of flower buds.

2. The method of claim 1, wherein the dicot plant is *Arabidopsis thaliana* and the dicot plant from (a) is selected for having an increased number of cells in the phloem of a vascular bundle of a first rosette leaf, for having an increased number of vascular tissues in a primary stem, or for having an increased number of phloems in at least one vascular tissue.

* * * * *